United States Patent
Rushbrooke et al.

(10) Patent No.: US 6,608,918 B1
(45) Date of Patent: Aug. 19, 2003

(54) METHOD AND APPARATUS FOR ASSAY ANALYSIS

(75) Inventors: John Gordon Rushbrooke, Cambridge (GB); Claire Elizabeth Hooper, Cambridge (GB); William Wray Neale, deceased, late of Cambridge (GB); by Ann Neale, personal representative, Cambridge (GB)

(73) Assignee: Packard Instrument Company, Inc., Meridien, CT (US)

( * ) Notice: Subject to any disclaimer, the term of this patent is extended or adjusted under 35 U.S.C. 154(b) by 0 days.

(21) Appl. No.: 09/284,325
(22) PCT Filed: Oct. 9, 1997
(86) PCT No.: PCT/GB97/02789
§ 371 (c)(1),
(2), (4) Date: Jul. 26, 1999
(87) PCT Pub. No.: WO98/15814
PCT Pub. Date: Apr. 16, 1998

(30) Foreign Application Priority Data

Oct. 10, 1996 (GB) ............................................. 9621122

(51) Int. Cl.[7] ................................................. G06K 9/00
(52) U.S. Cl. .................................. 382/133; 255/377.11
(58) Field of Search ................................. 382/133, 128; 377/10; 255/370.11

(56) References Cited

U.S. PATENT DOCUMENTS 5,828,067 A * 10/1998 Rushbrooke et al. .. 250/370.11
5,866,907 A * 2/1999 Drukier et al. ............. 250/328
5,885,530 A * 3/1999 Babson et al. ................ 422/63

* cited by examiner

Primary Examiner—Jayanti K. Patel
Assistant Examiner—Barry Choobin
(74) Attorney, Agent, or Firm—Barnes & Thornburg (57) ABSTRACT

The present invention provides a detection system comprising means (12) for supporting a multiple sample assay (11) in an inspection station, plural addressable photosensitive detector elements in an array (20) which is positioned relative to the inspection station, means (30, 32) for addressing the groups of elements at regularly occurring intervals of time so as to generate linked numerical values for analysis, means (44, 46) for computing the arithmetic mean of the linked numerical values read out, and means for supplying as output information the numerical value of the computed arithmetic mean of the linked values. A method of analyzing a multiple sample assay is also provided. In order to enable corrections for the effects of chemical or color quench, the system can be calibrated by performing a large number of exposures of at least part of the array to a sample of known, constant activity and having a known amount or concentration of quenching agent, and repeating this process for each of a number of other samples with differing amounts or concentrations of said agent. The photosensor outputs obtained in the course of these processes are statistically analyzed to provide an index from which look-up tables for color and/or chemical quench correction can be compiled.

25 Claims, 5 Drawing Sheets

METHOD AND APPARATUS FOR ASSAY ANALYSIS

FIELD OF INVENTION

This invention concerns screening systems and detection apparatus and methods for the inspection and analysis of multiple sample assays.

The invention concerns methods and apparatus for determining assay activity which results in the emission of photons and is of particular application to scintillation proximity assays, phosphorescence caused by the release of beta particles, liquid scintillation assays and luminescence assays (including chemi-luminescence, bio-luminescence and fluorescence), as well as cell-based assays, involving correlated bursts of photons. The invention is of particular application to assays in which the photon emission is relatively weak and in which discolouration or cloudiness in the liquid phase of the assay can inhibit the escape of photon emission to a detector. This interference with light transmission and/or reduction in efficiency in assay analysis is referred to as quench.

The invention is of particular application to the screening of multiple samples in pharmaceutical research and development using binding assay techniques and particularly scintillation proximity assays (SPA) using labelled beads or liquid scintillation counting using scintillation cocktails.

This invention may also be applied to correlated bursts of photons produced in luminescent assays, including cell based assays using luminescent labels indicators or substrates. These include enzyme linked assays, binding assay techniques and cell signalling assays (e.g. involving ion uptake and transport).

BACKGROUND TO THE INVENTION

Historically photon detection has been by way of a photomultiplier tube (PMT). Such devices have a very fast rise time and high resolution in the time axis and can respond to photon emission durations of a few nanoseconds. Consequently if such emissions are occurring at intervals of a few microseconds, an electrical signal can be produced which is proportional to the light incident on the photocathode and a count rate (ie number of emissions per unit time) for a particular sample can be determined by counting the pulses from the PMT over a given window of time. A PMT based counter known as the TopCount (Registered Trade Mark) is produced by the Packard Instrument Company of USA. Techniques associated with the use of such counters for quench correction are described in a paper entitled Quench and Quench correction in Top Count topics published by the Packard Instrument Company in July 1993. Quench correction as applied to scintillation proximity assays is dealt with in a later paper also published by Packard Instrument Company under the heading Top Count Topics of February 1994. The use of a liquid scintillation counter in the presence of quench is also described in U.S. Pat. No. 4,633,088.

Since there is no X Y information attributable to the output signals from a photomultiplier tube (PMT), such a device can only be used to view one sample at a time. Where a large number of samples have to be inspected, either a very long period of time must be allowed so as to enable the PMT to be positioned successively over each of the samples for a sufficiently long period of time to allow a scintillation count to be determined for each sample, or in the other extreme a correspondingly large number of separate photomultiplier tubes must be mounted one above each of the samples so that all of the samples can be inspected simultaneously. In practice a compromise has normally been arrived at, and where the number of samples is of the order of 100 arranged in rows and columns (for example 8 rows and 12 columns), a row of eight PMT's has been positioned above the array of samples so that the eight columns can be inspected simultaneously, and the row of PMT's has been indexed row by row along the twelve columns. If each investigation is of one minute duration, the total assay inspection time will be something of the order of 12 minutes. In the example quoted, the total time if only one PMT were involved would be 96 minutes.

The 8×12 array of 96 samples is typical of so-called well plates but recently there has been a trend to larger well plates containing some hundreds of sample wells per plate and there is a desire to introduce even larger well plates having 1,000 or more wells per plate. Multiple sample assays using "ink dot" techniques can have as many as 10,000 "dots" per assay. The cost and complexity of using the correspondingly large number of PMT's if assay times are to be kept low makes the manufacture of such an instrument unattractive and it is an object of the present invention to provide an alternative inspection system which is more sympathetic to large numbers of samples and which will allow overall assay inspection periods to be kept relatively short.

This last feature is of considerable importance where the chemistry of the assay is not sufficiently stable to allow a considerable period of time to elapse between the start and finish of an assay investigation.

Heavy demands are now being made on screening systems by developments in combinatorial chemistry and genomics. In these and other applications the phenomenon of quench can introduce errors. Quench occurs in liquid scintillation counting where specific components in the sample can interfere with the production and/or transmission of light. A reduced scintillation count results and unless steps are taken to correct for quench, it is impossible to say whether a low level of activity from a particular sample is due to low inherent photon emission (due for example to a lack of binding in the assay) or is due to the opacity of the liquid phase of the assay which inhibits the release of photons from what is otherwise a relatively active sample.

There are two recognised forms of quench.

Chemical quench occurs when the unwanted compound interferes with the scintillation or luminescence process causing non-radiative dissipation of energy. This reduces the apparent energy of the decay event and the number of photons produced.

Colour quench is an optical phenomenon whereby photons produced by the scintillation or luminescence process are absorbed by the unwanted material before reaching the detector.

OBJECT OF THE INVENTION

This invention seeks to provide a detection system and method of inspection for use with microplates containing hundreds or thousands of individual reaction wells or multiple site assays containing many hundreds or thousands of reaction sites, and seeks to provide an apparatus and method which will speed up the inspection and analysis of such assays relative to the time which would be required using conventional techniques.

The invention also seeks to provide an improved detection system and method by which the apparent reduction in activity from any one site or well caused by discolouration or greying of the sample (colour quench); or by interference with the photon emitting properties of the assay by the sample ingredients or by-products (chemical quench); or both, can be corrected.

In particular, it is an object of the invention to provide a detection and counting system which can be adapted to accommodate variation due to quench, so that the numerical count obtained is substantially independent of quench.

SUMMARY OF THE INVENTION

According to one aspect of the present invention a detection system embodying the invention comprises:

1. means for supporting a multiple sample assay in an inspection station,
2. plural addressable photosensitive detector elements in an array which is positioned relative to the inspection station so that light emitted from a sample impinges on a unique group of photosensitive elements, to produce a change in the electrical characteristics thereof, so that a change which is attributable to the group is associated with that sample, which change is permanent at least until the detector elements have been addressed and any change in their characteristics has been read out as an item of information,
3. means for addressing the groups of elements at regularly occurring intervals of time to generate the said items of information,
4. means for attributing a numerical value to the individual items of information,
5. means for storing the numerical values in such a manner that all the values which relate to any one of the samples are linked,
6. means for storing a sample identifier for each set of linked values,
7. means for reading out the linked values relating to a sample to permit computational analysis thereof,
8. means for computing the arithmetic mean of the linked numerical values read out, and
9. means for supplying as output information the numerical value of the computed arithmetic mean of the linked values, together with the sample identifier therefor.

Where the light emitted per sample is very low, an image intensifier is preferably provided between the samples and the photosensitive detector elements. Typically an image intensifier CCD camera is employed. Alternatively a cooled CCD camera may be used operating at the higher frame rates now achievable with these devices, typically in the range 0.1–10 frames per second.

According to another aspect of the invention a method of analysing a multiple sample assay comprises:

1. locating the multiple sample assay in an inspection station,
2. imaging light emitted from the samples onto a plural array of addressable photosensitive detector elements so that light emitted from a sample impinges on a unique group of the photosensitive elements to produce a change in the electrical characteristics thereof so that a change attributable to the group is associated with that sample, which change is permanent at least until the elements have been addressed and any change in their characteristics has been read out as an item of information,
3. addressing the elements at regularly occurring intervals of time to generate the said items of information,
4. converting each item of information into a numerical value,
5. storing the numerical values in such a manner that all the values which relate to any one of the samples are linked.
6. generating and storing a sample identifier for each set of linked values,
7. reading out the linked values relating to a sample and computing the arithmetic mean of the linked numerical values, and
8. supplying as output information the numerical value of the computed arithmetic mean of the linked values, together with the sample identifier therefor.

Where the light emitted per sample is very low the method may include the step of image intensifying the light between the sample and the photosensitive detector elements, or a cooled CCD may be used.

The method may include the step of filtering the light between the samples and the detector element array.

The improved system and method is of particular use in assays in which the light emitting entity has a well defined probability of emitting a given number of photons per unit period of time, and in which there are many occasions when the entity emits two or more detected photons per disintegration. Examples of such assays in which the light emitting components of each sample have a well defined probability for emitting a given number of photons per initiating event are radio isotope labelled assays using for example Tritium or Carbon 14. Here there are equivalent well defined probabilities $P_0$, $P_1$, $P_2$, $P_3$ etc, of detecting 0, 1, 2, 3 . . . photoelectrons per radioisotope disintegration. The actual probabilities of course depend on the particular isotope, SPA bead (in the case of scintillation proximity assays); the scintillant; the optics; and the characteristics of the camera. Equivalent probabilities might be defined for the correlated emission of photons by a cell, proceeding via processes such as cell signalling, generation of ion fluxes, or enzyme activity, which are linked to luminescent signals.

Preferably at each addressing step each photosensitive detector element is reset to an initial state ready to begin receiving light again.

Preferably in such an arrangement the detector elements and operating conditions are selected so that the changes in electrical characteristics are linearly proportional or nearly so to the quantity of light incident thereon.

Preferably, before the system is used, a calibration step is performed in which samples of known activity are presented to the array of photosensitive elements, using an appropriate addressing time interval, so that output information from each sample-detector pair is available.

By using different samples of known concentrations of calibrated light emitting material such as Microspheres as produced by Arnersham International plc to vary the activity level in different samples, and performing a series of tests on these different known activities, so the observed numerical output information from the groups of detector elements in response to the different known activities can be logged against the known activity in a first calibration memory, to provide a look-up table for converting future numerical output information to sample activity.

Preferably each group of detector elements is subjected to a large number of exposures so as to obtain a large number of different outputs therefrom in each of the aforementioned tests before the mean numerical value attributable to any particular sample/detector group combination is computed.

Calibration may be speeded up by computing the mean value after each exposure and comparing each computed mean with the accumulating mean value (computed from all previous output information for the test from that detector group), and stopping that sequence of exposures and computations when the comparison indicates a desired level of similarity between the two computed mean values.

The process may be stopped for each detector group individually or may be continued until all the computed mean value comparisons for all the detector group has achieved the similarity criterion.

Any difference between the final accumulation mean value for each detector group and a theoretical expected mean value for the test may for example be stored as detector group response variations in a supplementary calibration memory.

In the preferred system, albeit requiring a large number of individually addressable photosensitive detectors in the detector array, each group contains a relatively large number of photosensitive detector elements so that light from the associated sample will now fall on some of this large number of adjacent photosensitive detector elements in the group.

A preferred photo detector element array is an image intensified integrating CCD. Such devices can be obtained with an array having a large number of individually addressable detector elements arranged in rows and columns.

For example using a 385×288 chip, when part of an 864 well plate is viewed, each of the wells can be typically associated with a respective 20×20 group of pixels on the camera chip.

Devices are available having nominally 3000 rows and nominally 2000 columns of photosensitive elements, ie a nominal total of 6,000,000 elements and such a device can permit up to 10,000 appropriately arranged samples to be imaged each sample having available to it a group of 25×25 pixels.

Thus in such a device, light emanating from a sample will result in some of the pixels in its associated 25×25 group of pixels changing state, and generating an appropriate output signal at the end of the frame interval as the camera chip is read out. The change of state of these pixels is caused by the detection of a single photon, and the flux of photons on the array can be sufficiently low for it to be very unlikely that these pixels will receive more than one photon during a single frame, even though a 25×25 group of pixels may receive many photons during a frame. Thus, the more light (i.e. the larger the number of emitted photons) that has emanated from a sample well the greater is likely to be the number of individual pixels in the corresponding 25×25 array which will have registered incident light, and therefore the greater the number of "change of state" transitions which will be counted at the end of that frame interval for that sample to be linked with the sample identifier.

By way of example the input area of a 40 mm camera is typically 32×24 mm², but in accordance with another feature of the invention this can be increased using optical devices based on lenses or fibre optic tapers or both, so as to receive light from a sample plate occupying a larger area.

A filter may be incorporated between the samples and the image intensifier to remove unwanted wavelengths.

The separate pixels in each 25×25 group can be individually addressed, and since the likelihood of light from any one sample impinging on the same pixel in the relevant group during a typical frame period of 10 milliseconds is very low, the individual detector elements of a CCD camera chip can be considered to be substantially bistable devices which are reset at the end of each frame period, and whose state at the end of each exposure (frame) is either low or high depending on whether or not light has impinged thereon. If low, light energy has been incident on the pixel and when it is scanned during read-out, an output information signal indicating this is produced as each such pixel is reset. Using an integrating CCD camera chip having a defined frame period (ie interval between read-outs) each group of pixels will acquire light from its related sample during each frame period and if it is assumed that r photoelectrons are detected per frame by the group (where r is greater than or equal to zero) then at the end of each frame the frame store associated with the chip is provided with another value of r for that group. Since each group corresponds to one of the samples in the array under analysis, a sample identifier can be associated with each of the string of values of r from each group, which is available to be linked with the mean value computation for the string of values r.

Hence, the number of photons emitted from a sample region per frame is measured for each of a succession of (for example 5000) frames. This enables a frequency distribution of detected photons to be calculated. It will be appreciated that, in this context, the term "frequency" refers to the number of photons emitted per unit time, not the intrinsic frequency of each photon.

Preferably a CCD camera chip is selected which employs charge transfer thereby speeding up the read-out of the array. In such devices a second "hidden" array of elements is provided in addition to the primary array, and the charge condition in each row of the first array is transferable in parallel into a corresponding row in the second array on receipt of a reset signal at the end of each frame interval, the reset signal serves to restore the charge in each of the detector elements of the primary array and this allows the whole of the following frame interval for reading out the charge pattern of the secondary array.

The first calibration step described above, allows a look-up table to be created of sample activity against mean numerical value per sample-group pair. This calibration step is necessary before a CCD camera can be used on unknown assay samples.

Second and third calibrations are also necessary if quench can affect future (unknown) assay samples to be imaged and analysed.

The first of these additional calibrations allows activity level measurement to be corrected for colour quench. The look-up table needed is compiled as follows:

Using an imaging device as aforesaid, a large number of exposures (frames) are performed using samples of constant (known) activity and having different (known) dye concentrations, and from each set of results the mean number of detected photons per frame from a sample ($M_1$) and the variance ($V_1$) about the mean are computed and a first Index ($I_1$) is computed using the formula $(V_1-M_1)/M_1$. The computed value of $I_1$ for each different dye concentration allows the look-up table to be compiled, for colour quench correction.

The mean and variance and formula for computing the index may be adjusted to compensate for random background photons, as occur with phosphorescence from the sample plate background and with the intrinsic autofluorescence found in cell-based assays.

The other additional calibration allows activity level measurement to be corrected for chemical quench, and another look-up table is created in the same way. Thus samples of constant (known) activity having different (but known) concentrations of a chemical quenching agent such as nitro-methane are imaged over many frames, and the mean ($M_2$) and variance ($V_2$) of the results are computed to provide a second index $I_2$ for different nitro-methane concentrations, to generate a chemical quench correction look-up table, using the formula $I_2=(V_2-M_2)/M_2$.

The "Colour quench correction" look-up table constitutes the second calibration, and the "Chemical quench correction" look-up table constitutes the third calibration referred to above.

Disregarding quench (and other factors which can affect the number of photons emitted in response eg to radio isotope disintegration), to a first approximation the change in charge in any photosensitive elements in a CCD camera array and hence the number of detected photons will be a measure of the radioisotope or luminescent activity in the sample. Where this measured activity is affected by the underlying process being determined in the sample (eg binding) then this activity will also therefore correspond to the degree of binding which is occurring in the sample which is imaged thereon. In general relatively small amounts of light will be emitted from a sample in response to each radioisotope disintegration and these will on average occur at relatively well spaced intervals, although lasting individually for very short periods of time.

The photon emission from a single Tritium disintegration per sample per CCD exposure period typically will result in only a handful of detected photoelectrons (typically in the range 1–10). The number can be increased using an image intensifier before being supplied to a CCD chip.

Using a cooled CCD, instead of an image intensified CCD camera, only the handful of photoelectrons would be available to the CCD chip, but by operating such a cooled CCD camera in the range 0.1–10 frames per second, there may be sufficient information available to allow the present invention to be performed, as the output signals from the CCD.

Where higher photon producing assays are used the intensifier may be gated, so as to reduce the number of photoelectrons reaching the CCD chip or image intensifier CCD camera to prevent saturation or damage.

For each gate setting the camera or intensifier-camera combination can be calibrated by using samples of known activity.

EXAMPLE

In the case of SPA assays, calibrated radioisotope labelled microbeads can be obtained from Amersham Intentional plc and a range of samples created having different concentrations of active heads. By exposing the image intensifier—CCD camera combination to samples of known concentrations, and therefore predicted levels of activity, so the electrical signals obtained from the sample related groups of pixels in the CCD array, for different known activity levels, can be ascertained and recorded for subsequent comparison in a first look-up table, see FIG. 1. For other assays, such as luminescent linked enzyme activity or cell-based assays, the units of activity would refer to enzyme activity or units of ion or substrate concentration.

Where quench is occurring, either colour quench where some of these photons are absorbed by the super-natant liquid in a sample region before they can be detected, or chemical quench where the number of photons produced is lowered because of chemical interference, there is apparently lower activity and CCD read out signals of the relevant sample-related groups of pixels will therefore be less than would have been the case with no quench occurring.

A second look-up table to permit another level of calibration is therefore required.

This is produced by adding different (known) concentrations of a colouring agent (normally Tartrazine) to each of a plurality of samples having the same (known) level of photon activity (using eg calibrated microbeads as aforesaid) and noting the numerical values corresponding to the electrical signals obtained from each sample-related group of pixels, in the CCD camera array, for each of a number of successive exposures. From each set of values the arithmetic mean M and the variance V are computed. $M_O$ and $V_O$ are the values where no colouring agent is present, whilst $M_N$ is the general representation of the arithmetic mean from a sample having a known concentration $C_N$ of Tartrazine.

A transmission Index I is also computed for each sample using the formula $$I=(V-M)/M$$

Where appropriate these values of M and V can be corrected for any background and noise contribution by subtracting appropriate values of $M^1$ and V where $M^1$ and $V^1$ are the mean and variance values obtained when the only signals received by the CCD camera can be attributed to background and noise. Such a correction may be appropriate where plate or sample phosphorescence has been caused prior to the assay, for example by exposure to light.

For each value of concentration $C_N$, of the colouring agent the computed value of a transmission coefficient $T_N$, (obtained from the measured value of $M_N$ and the previously measured value of $M_O$) can be plotted.

Figure 2:
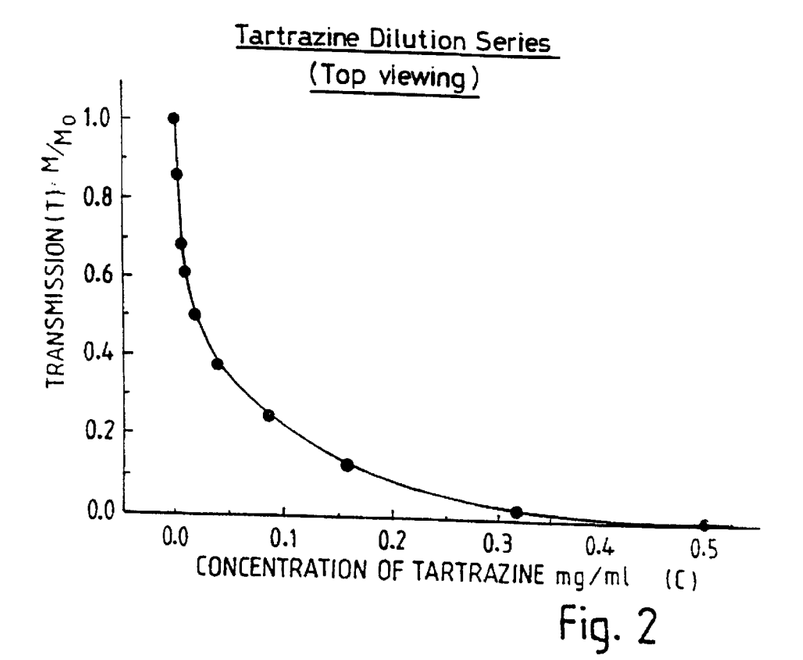
Figure 3:
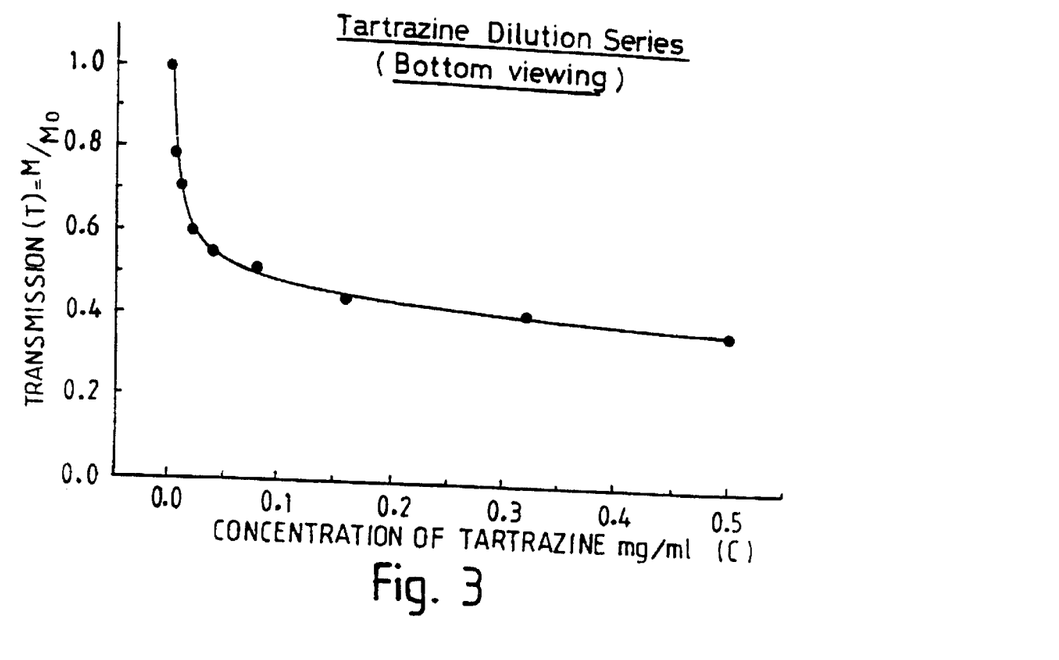

A typical plot of T against C for a top viewed sample is shown in FIG. 2.

Where a sample is viewed from below, the quench only significantly alters the light which is reflected back through the sample from the top of the well and/or the liquid air interface. A typical Plot if the sample is bottom viewed is shown in FIG. 3.

Using $M_O$ (ie the mean value M when the concentration of Tartrazine is O), all other values of M, $M_N$ (for increasing concentrations of Tartrazine), can be normalised by dividing each value of $M_N$ by $M_O$. For convenience the normalised values of M will be referred to as the Transmission CT) of each sample, where $T_N=M_N/M_O$.

Figure 4:
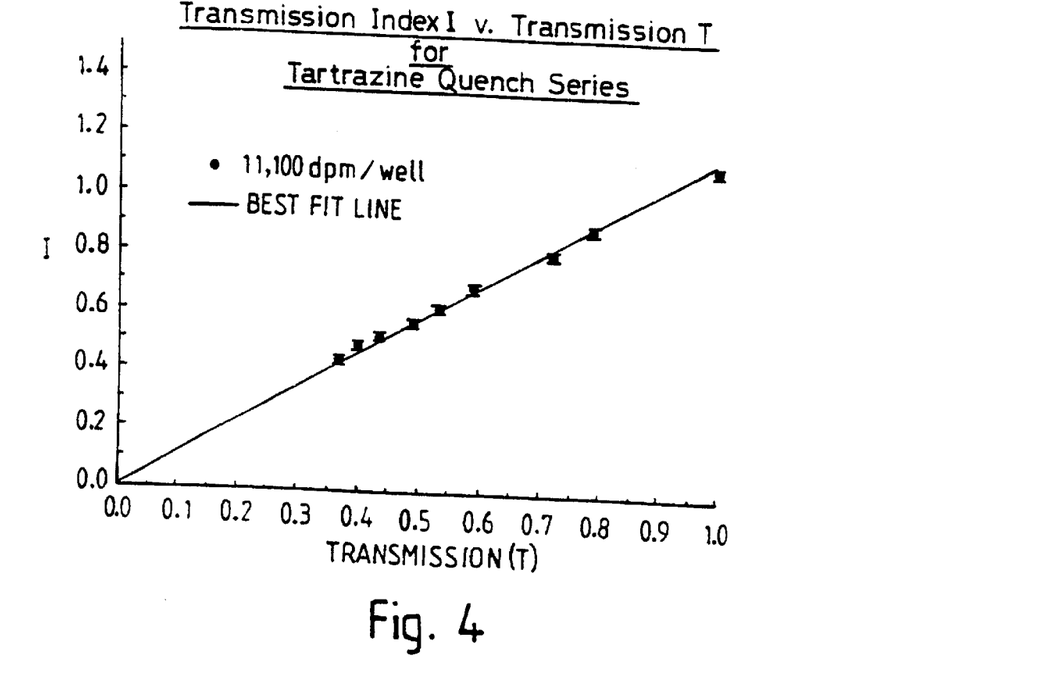

If the value of I is plotted against the value of T for each sample, it is found that the variation of I to T is essentially a straight line (See FIG. 4). The second look-up table can be compiled from this graph.

The true activity of an unknown sample can be determined by applying the two calibrations obtainable from the two look-up tables, in the following manner:

(A) The mean and variance of the numerical values of the CCD output signals obtained by reading the particular CCD pixels relating to the sample, are computed from a large number of successive exposures (frames).

(B) The value of I from the unknown sample is computed using the formula I=(V–M)/M and the corresponding value for T is found from the second look-up table (FIG. 4).

(C) Using this value of T, the mean numerical value M already obtained from (A) above is increased using the formula $M_{NEW}=M/T$.

Figure 1:
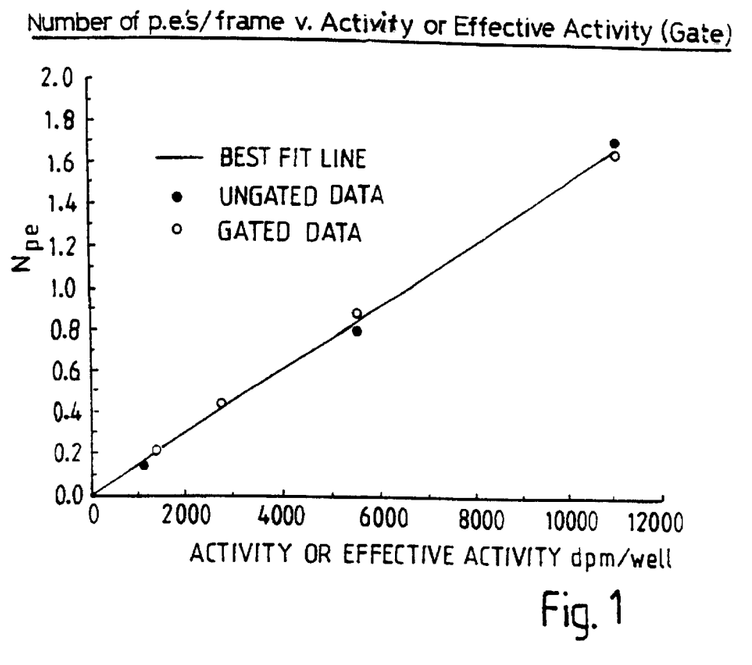

(D) Using the new value of M, ($M_{NEW}$), the value of activity corresponding thereto is observed using the first look-up table (FIG. 1). This value of activity is used as the true activity value for the sample, and is supplied together with the sample identifier as the corrected output signal for the sample concerned.

By using a high speed computer, the mean and variance can be computed from the succession of numerical values obtained during the scanning of the separate groups of pixels (each group corresponding to one of the samples), and the value of I can be computed for each set of values corresponding to each sample. The value of T can be obtained for each sample using the FIG. 2 look-up table and the corresponding value of activity $A_1$, $A_2$ etc obtained from the FIG. 1 look-up table, for each sample $S_1$, $S_2$ etc, so that the corrected values $A_1$ $A_2$ ... $A_N$ for all samples $S_1, S_2 ... S_N$ in a multi-sample assay having N samples, can be outputted directly.

If other corrections such as for background noise etc, are to be employed, these should be applied at the appropriate point to correct the numerical values to be used in addressing or compiling the look-up table.

EXAMPLES OF APPARATUS

Figure 6:
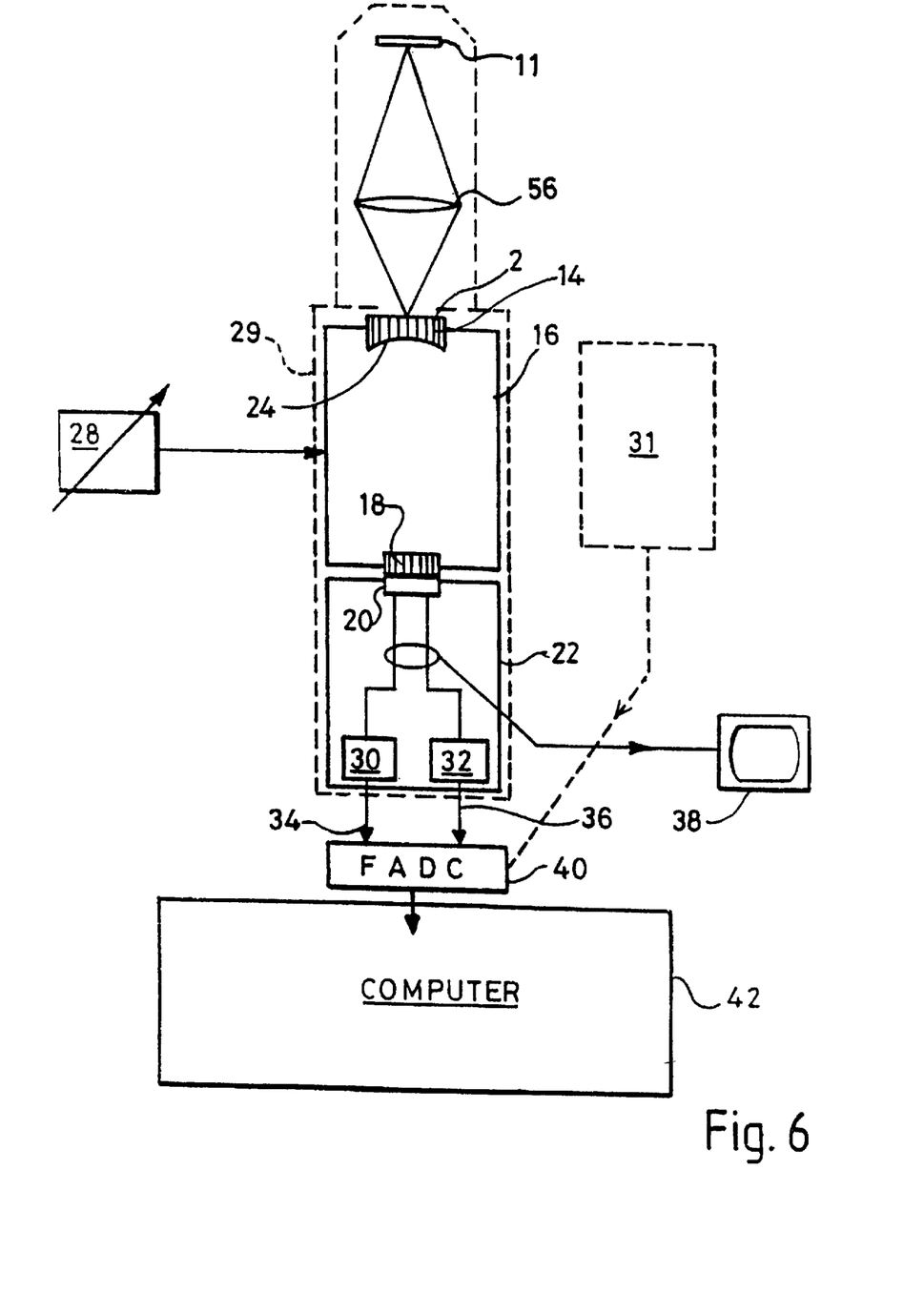

FIG. 6 shows how a multiwell plate 12 can be imaged. In this example an intensified CCD camera combination 16/22 is used, although it will be appreciated that a cooled CCD camera may be employed if preferred and if the signal levels are appropriate. Signals obtained from each read out of the CCD array 20 are transferred by the addressing electronics to a fast ADC 40 and via preprocessing and video compression circuits 52 to a computer bus 54 containing first processor 44, bus memory 46 and a large capacity hard disc drive 48.

The processor and related memory is programmed to compute from the numerical values supplied to it from the FADC 40, the mean and variance for each string of values from each of the groups of pixels in the CCD array 20 identified by the addressing electronics 30, 32 as corresponding to different samples in the multiwell plate 12.

Since the plate may not be identically aligned with the optical/scanning system, a first calibration step may be employed in which light is projected through the well-plate and into the image intensifier 16 so as to form a pattern of the wells on the CCD array 20. By using a suitable wavelength light, possibly by using filters, so the wells can be strongly illuminated and the walls of the wells will appear dark. The resulting pattern can be interrogated in known manner and X, Y information derived from the CCD output signals for storing in a memory (eg memory 46) for use in subsequent scans of the CCD array to identify the groups of pixels in the array corresponding to the different samples.

The apparatus may include means for forming an image of a sample array on the photosensitive detector array prior to measurements being made on the sample activities, to permit the CCD array to be calibrated on an X, Y basis (or any other spatial coding basis), and to enable an X, Y image to be generated for use in identifying the positions of pixel groups corresponding to the different samples to be interrogated.

When using the method of analysing a multiple sample assay as aforesaid a preliminary step can be included, involving the formation of an optical image of the samples on the photosensitive detector array to enable an X, Y map of the group of elements which correspond to the region of the detector array which will be exposed to the different samples, and the X, Y coordinates stored in a memory for subsequent use as the detector elements are read out at the end of each exposure of the detector array to light emissions from the wells during the investigation.

In one arrangement the CCD array X-Y mapping may be achieved by placing a similar multiple sample assay in place of the one to be analysed, in which each sample contains a large number of high photon emission material (eg Amersham calibration microbeads) and the light pattern obtained on the detector array is used to generate the X, Y map of the samples which will be presented to the array when a similar multiple well assay is substituted for the first. In this arrangement means is provided for aligning the assays accurately with the image intensifier window such as 14 in FIG. 5.

Figure 5:
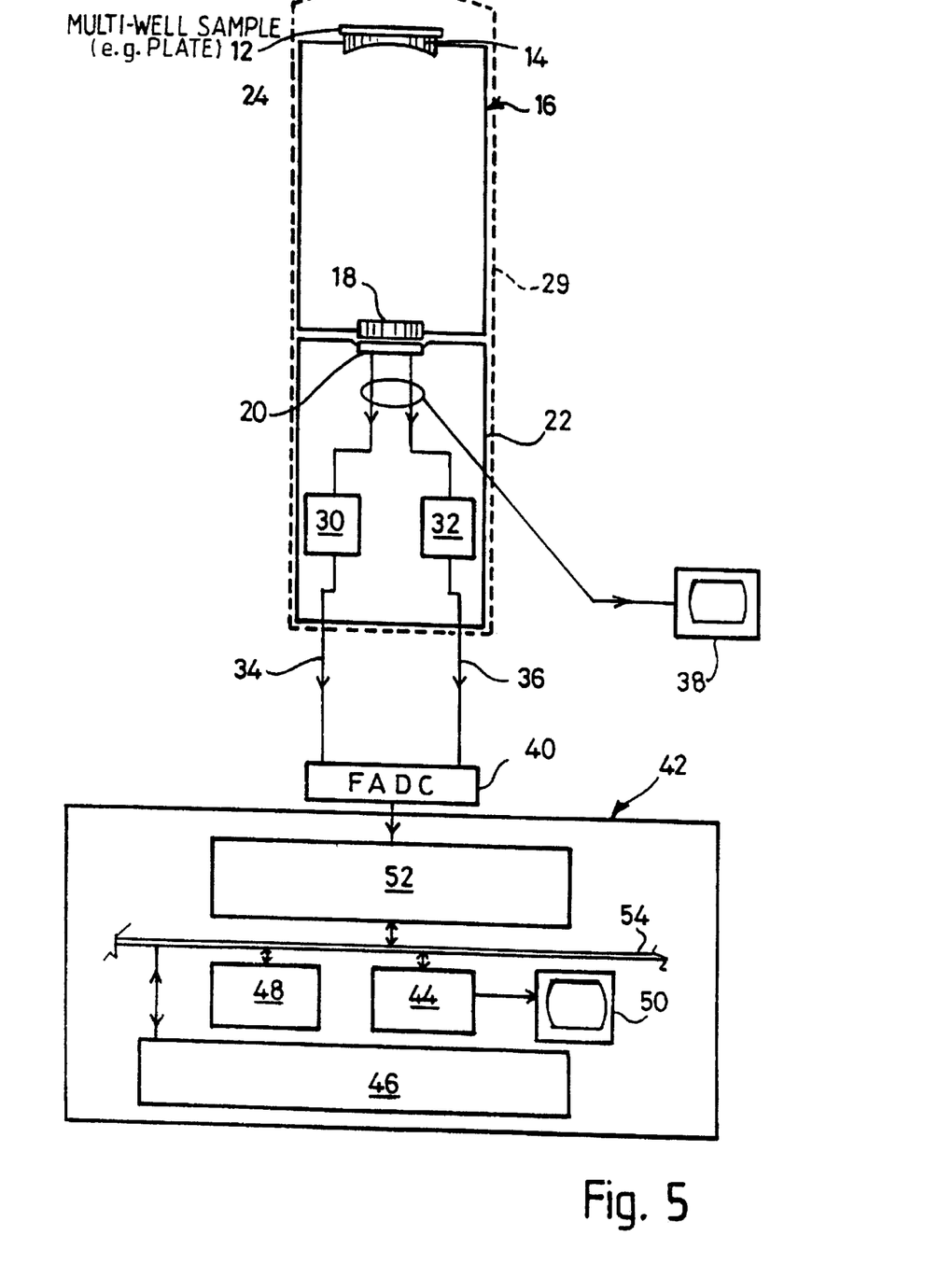

A second arrangement is shown in FIG. 5 in which a lens 56 projects an image of a multiple sample assay 11 onto the input widow of an image intensifier 14. The rest of the embodiment is as described above, except that in this case the image intensifier is shown as being controlled by 28 which gates the input/output pattern to enable higher photon activity samples to be used without saturating the CCD 20.

For operation of the circuits and the identification of the centroids of clusters of activated pixels in the CCD array and other signal processing data relating to read out of the CCD, reference is made to copending applications GB 2,294,319A and WO95/11461.

Figure 7:
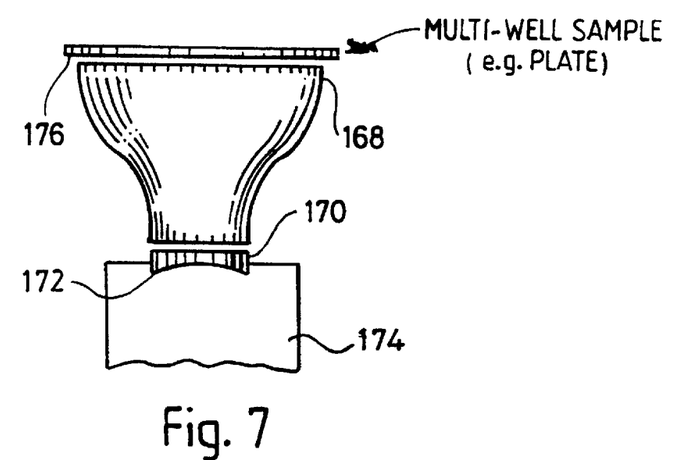

FIG. 7 shows how a fused fibre optic taper can be used to allow a large area well plate 176 to be contact-imaged via a smaller image intensifier input window 170. As an alternative to a fused fibre optic taper, an arrangement of separate fibre optic channels can be used to allow a large area to be thus contact-imaged.

Figure 8:
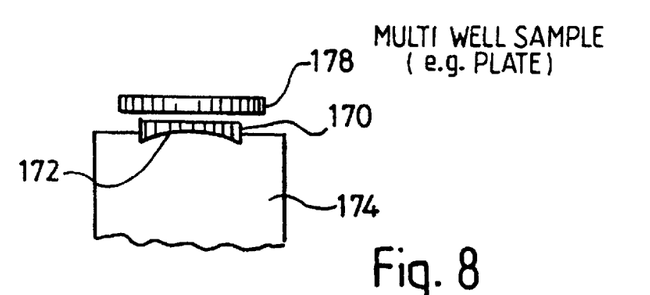

FIG. 8 shows how a well plate 178 can be contact imaged directly to the window 170.

Figure 9:
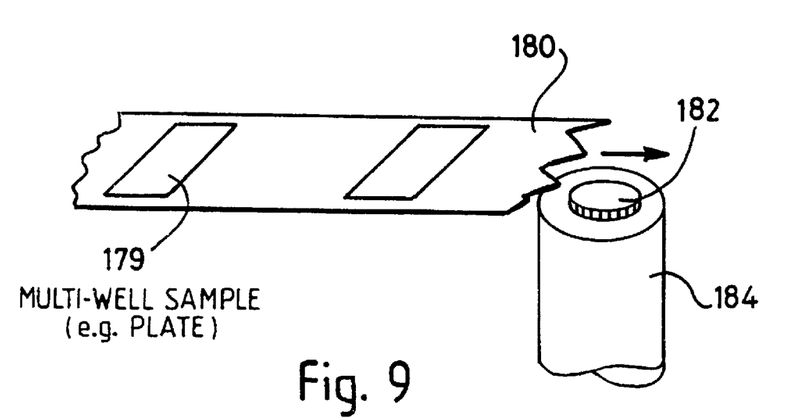

FIG. 9 shows how a succession of multiwell plates such as 179 on conveyor 180 can be presented in turn to the input window 182 of an image intensifier/CCD camera combination 184, for contact imaging via the window.

It has been observed that where photon activity is related to the binding of assay components to labelled micro beads, the latter will tend to migrate to the bottom of the wells, and the effects of quench can be reduced if the photon activity is observed through a transparent base of each well rather than looking down through the liquid phase of the sample, by so-called top-viewing.

It will be noted that in all the arrangements illustrated the samples are viewed from below. This is not essential, and in some cases is not possible, in which case the more conventional "top viewing" must be employed in which event the light emitted may be much more affected by quench. However where bottom viewing is possible, this means that a substantial percentage (typically 20–40%) of the available light from the binding sites will exit, substantially unaffected by quench, through the well base.

Where the sample support plate (eg well plate) produces a background level of photon emission (e.g. plate phosphorescence), a narrow band filter may be employed to reduce wavelengths of the unwanted background emissions, in addition to, or instead of, producing a background emission count value ($M_{BACKGROUND}$) and reducing future values of M by this amount.

Where bottom viewing is to be employed, the supernatant liquid in the samples may be deliberately darkened or blackened so as to reduce the reflection of light from the top or sides of the well/sample. This will substantially restrict the emitted light to that which is emitted from the binding sites in the general direction of the bottom of the well (typically 20 to 40% of the total light emitted by the binding sites). This removes much of the uncertainty arising from quench in the assay but reduces the light available to the camera.

To correct for quench, either colour quench where some of the photons are absorbed by the super-natant liquid in a sample region before they can be detected, or chemical quench where the number of photons produced is lowered because of chemical interference, the frequency distribution of the number of photons detected from a given sample region per frame is measured from a collection of frames (typically 5000). As well as finding the mean (M) of this frequency distribution, the variance (V) about the mean for a sample region is also measured. A transmission index I is then computed from the formula I=(V−M)/M, as described above, and the index used via a look-up table to make a correction for quench. Note that this correction implies finding the fraction of photons that are being detected (the "transmission" T), compared to the number that would have been detected in the absence of quench. For assays like SPA it is found that to a reasonable degree of accuracy I depends linearly on T.

In addition to I, further transmission indices can be defined in terms of higher moments of the frequency distribution.

These further transmission indices are defined by the following formulae:

$$J=(W-3V+2M)/(V-M)$$

$$K=(X-6W-3V^2+11V-6M)/(W-3V+2M)$$

In these expressions M is the first moment about zero, and V, W and X are respectively the second, third and fourth moments (as customarily defined) about the mean, of the frequency distribution.

Each of these indexes, I, J and K depends in a simple way (almost linearly) on the transmission T. A look-up table for each can be used to make a separate quench correction.

In measuring assays a common source of background is plate or sample phosphorescence caused by activation prior to the assay, e.g. by exposure to light. Another source of background is the intrinsic autofluorescence found in cell-based assays. Unlike the correlated bursts of photons coming from the sources in a sample region in the case of SPA or other assays, these background photons are random, single photons, i.e. they have a Poisson frequency distribution represented by a mean number B of photons detected per frame from a sample region. One can show that in the presence of such a Poisson background of strength B, I becomes (V−M)/(M+B), but J and K are unaffected. It follows that for a given sample the value of T derived from I might be significantly different from that derived from J or K. This fact would reveal the presence of plate or sample background and obviously provide a method of finding B, since B is the quantity that has to be subtracted from the denominator of I to bring I into conformity with J or K. The mean number of photons per sample region per frame could then be corrected for background B before using the look-up table to find the activity of the sample.

Where the proximity of the labelled beads can produce additional photon activity, a further calibration may be made and a further look-up table created using the same parameters of M and V, but now from the signals relating to samples having known, different concentrations of calibrated beads, all settled at the base of their respective sample wells. The photon emissions created without the presence of labelled assay components is observed and the I, J or K values computed for the different concentrations, normalised as before, and when unknown assays are analysed subsequently, in which the concentration of labelled microbeads is nevertheless known, the numerical values obtained for the unknown samples may be reduced by subtracting the photon activity noted as being attributable to bead proximity for that concentration, from the actual activity noted for the sample, or by proportioning the actual activity by an index derived from the noted values caused by proximity emissions.

The problem of quench can be solved simply by bottom viewing (with or without corrections for background and bead proximity), in which case no second look-up table (as defined above) may be required. In the case of quench affected bottom viewing the methods previously described for producing and using the second look-up table may be used.

Where the activity of the samples is such that all activity should produce sufficient photons to cause a distribution of photoelectron events in an image intensifier which includes two or more photoelectron emissions during some of the read outs from each sample, a threshold may be applied to the numerical values from which the mean and variance (if required) are to be computed for each sample, so as to eliminate numerical values corresponding eg to only 1 photoelectron per sample/per frame, so that only frames with 2 or more photoelectron emission activities are used in the computation. This helps reduce influence of background.

Such a threshold would be used where the isotope is Tritium. Higher thresholds might be employed for higher energy isotopes such as Carbon 14.

What is claimed is:

1. A method of analysing a sample assay, the method comprising the steps of:

(A) locating the multiple sample assay in an inspection station, (B) imaging light emitted from samples onto a plural array of addressable photosensitive detector elements so that light emitted from a sample impinges on a unique group of the photosensitive elements to produce a change in the electrical characteristics thereof so that a change attributable to the group is associated with that sample, which change is permanent at least until the elements have been addressed and any change in their characteristics has been read out as an item of information, (C) addressing the elements at regularly occurring intervals of time to generate the said items of information, (D) converting each item of information into a numerical value, (D) storing the numerical values in such a manner that all the values which relate to any one of the samples are linked, (F) generating and storing a sample identifier for each set of linked values, (G) reading out the linked values relating to a sample and computing the arithmetic mean of the linked numerical values, and (H) supplying as output information the numerical value of the computed arithmetic mean of the linked values, together with the sample identifier therefor, in which a first calibration step is performed in a series of tests on the groups of detector elements using different samples of known activities, the observed numerical output information from the groups of detector elements in response to the different known activities being logged against the known activity in a first calibration memory so as to provide a look-up table for converting future numerical output information to sample activity; and in which a second calibration step is performed to allow correction for colour quench, the second calibration step comprising performing a large number of exposures of at least part of the array of photosensitive detector elements to samples of constant known activity and having different known dye concentrations, computing from the exposure results the mean and one or more characteristics of the statistical distribution of the amount of light detection per exposure, and computing from said mean and one or more characteristics an index for each known sample, so as to enable look-up table for correction for colour quench correction to be compiled.

2. A method according to claim 1, wherein the method includes the step of image intensifying the light between the sample and the photosensitive detector element.

3. A method according to claim 1, wherein the method includes the step of filtering the light between the samples and the detector element array.

4. A method according to claim 1, wherein at each addressing step each photosensitive detector element is reset to an initial state ready to begin receiving light again.

5. A method according to claim 1, wherein the detector elements and operating conditions are selected so that the changes in electrical characteristics are linearly proportional, or nearly so, to the quantity of light incident thereon.

6. A method according to claim 1, wherein the second calibration step comprises performing a large number of exposures using samples of constant known activity and having different known dye concentrations, computing from sets of exposure results a mean ($M_1$) and a variance ($V_1$), and computing a first Index ($I_1$) using the formula $I_1=(V_1-M_1)/M_1$ so as to compile a look up table for colour quench correction.

7. A method according to claim 1, wherein the second calibration step comprises performing a large number of exposures using samples of constant known activity and having different known dye concentrations, computing from sets of exposure results the mean ($M_1$), the variance ($V_1$) and the third moment ($W_1$) about the mean, and computing an Index ($J_1$) using the formula $$J_1=(W_1-3V_1+2M_1)/(V_1-M_1)$$

so as to compile a look-up table for colour quench correction.

8. A method according to claim 1, wherein the second calibration step comprises performing a large number of exposures using samples of constant known activity and having different known dye concentrations, computing from sets of exposure results the mean ($M_1$), the variance ($V_1$), the third moment ($W_1$) about the mean, and the fourth moment ($X_1$) about the mean, and computing an Index ($K_1$) using the formula $$K_1=(X_1-6W_1-3V_1^2+11V_1-6M_1)/(W_1-3V_1+2M_1)$$

so as to compile a look-up table for colour quench correction.

9. A method according to claim 1, wherein the first calibration step is adapted to compensate for background photons, wherein background is determined from measurement of a sample with zero activity.

10. A method according to claims 1, wherein a further calibration step is performed to allow correction for chemical quench, this further calibration step comprising imaging samples of constant known activity but having different known concentrations of quenching agent over many frames, computing a mean and one or more characteristics of the statistical distribution of the results of said imaging, for each sample computing an index from said mean and characteristics so as to enable a look-up table of chemical quench corrections to be compiled.

11. A method according to claim 10, wherein the further calibration step comprises imaging samples of constant known activity having different known concentrations of a chemical quenching agent such as nitro-methane over many frames, computing a mean ($M_2$) and a variance ($V_2$) of the imaging results to produce a second index $I_2$ using the formula $I_2=(V_2-M_2)/M_2$ so as to compile a look-up table for chemical quench corrections.

12. A method according to claim 10, wherein the further calibration step comprises imaging samples of constant known activity having different known concentrations of a chemical quenching agent such as nitro-methane over many frames, computing a mean ($M_2$) and a variance ($V_2$) and third moment ($W_2$) about the mean of the imaging results to produce a further index $J_2$ using the formula $$J_2=(W_2-3V_2+2M_2)/(V_2-M_2)$$

so as to compile a look-up table for chemical quench correction.

13. A method according to claim 10, wherein the further calibration step comprises imaging samples of constant known activity having different known concentrations of a chemical quenching agent such as nitro-methane over many frames, computing a mean ($M_2$) and a variance ($V_2$), a third moment ($W_2$) about the mean and a fourth moment ($X_2$) about the mean of the imaging results to produce a further Index $K_2$ using the formula $$K_2=(X_2-6W_2-3V_2^2+11V_2-6M_2)/(W_2-3V_2+2M_2)$$

so as to compile a look-up table for chemical quench correction.

14. A method according to claim 1, wherein each group of detector elements is subjected to a large number of exposures so as to obtain a large number of different outputs therefrom in each of the aforementioned tests before the mean numerical value attributable to any particular sample/detector group combination is computed.

15. A method according to claim 14, wherein the mean value is computed after each exposure and compared with the accumulating mean value, and the sequence of exposures and computations stopped when the comparison indicates a similarity criterion between the two computed mean values is reached.

16. A method according to claim 14, wherein any difference between the final accumulation mean value for each detector group and a theoretical expected mean value for the test is stored as detector group response variations in a supplementary calibration memory.

17. A method according to claim 8, whereby the presence of background B, such as that due to plate or sample phosphorescence or from intrinsic auto-fluorescence in the case of cell based assays, is detected and corrected for, by comparing the value of the transmission T derived from the index I with that derived from either J or K.

18. A method of analysing a multiple sample assay, the method comprising the steps of:

(A) locating the multiple sample assay in an inspection station, (B) imaging light emitted from samples onto a plural array of addressable photosensitive detector element so that light emitted from a sample impinges on a unique group of the photosensitive elements to produce a change in the electrical characteristics thereof so that a change attributable to the group is associated with that sample, which change is permanent at least until the elements have been addressed and any change in their characteristics has been read out as an item of information, (C) addressing the elements at regularly occurring intervals of time to generate the said items of information, (D) converting each item of information into a numerical value, (E) storing the numerical values in such a manner that all the values which relate to any one of the samples are linked, (F) generating and storing a sample identifier for each set of linked values, (G) reading out the linked values relating to a sample and computing the arithmetic mean of the linked numerical values, and (H) supplying as output information the numerical value of the computed arithmetic mean of the linked values, together with the sample identifier thereof in which a first calibration step is performed in a series of tests on the groups of detector elements using different samples of known activities, the observed numerical output information from the groups of detector elements in response to the different known activities being logged against the known activity in a first calibration memory so as to provide a look-up table for converting future numerical output information to sample activity, and in which in a further calibration step is performed to allow correction for chemical quench, this further calibration step comprising imaging samples of constant known activity but having different known concentrations of quenching agent over many frames, computing a mean and one or more characteristics of the statistical distribution of the results of said imaging, for each sample computing an index from said mean and characteristics so as to enable a look-up table of chemical quench corrections to be compiled.

19. A method according to claim 18, wherein the further calibration step comprises imaging samples of constant known activity having different known concentrations of a chemical quenching agent such as nitro-methane over many frames, computing a mean ($M_2$) and a variance ($V_2$) of the imaging results to produce a second index $I_2$ using the formula $I_2=(V_2-M_2)/M_2$ so as to compile a look-up table for chemical quench corrections.

20. A method according to claim 18, wherein the further calibration step comprises imaging samples of constant known activity having different known concentrations of a chemical quenching agent such as nitro-methane over many frames, computing a mean ($M_2$) and a variance ($V_2$) and third moment ($W_2$) about the mean of the imaging results to produce a further index $J_2$ using the formula $$J_2=(W_2-3V_2+2M_2)/(V_2-M_2)$$

so as to compile a look-up table for chemical quench correction.

21. A method according to claim 18, wherein the further calibration step comprises imaging samples of constant known activity having different known concentrations of a chemical quenching agent such as nitro-methane over many frames, computing a mean ($M_2$) and a variance ($V_2$), a third moment ($W_2$) about the mean and a fourth moment ($X_2$) about the mean of the imaging results to produce a further Index $K_2$ using the formula $$K_2=(X_2-6W_2-3V_2^2+11V_2-6M_2)/(W_2-3V_2+2M_2)$$

so as to compile a look-up table for chemical quench correction.

22. A method according to claims 18, wherein each group of detector elements is subjected to a large number of exposures so as to obtain a large number of different outputs therefrom in each of the aforementioned tests before the mean numerical value attributable to any particular sample/detector group combination is computed.

23. A method according to claim 22, wherein the mean value is computed after each exposure and compared with the accumulating mean value, and the sequence of exposures and computations stopped when the comparison indicates a similarity criterion between the two computed mean values is reached.

24. A method according to claim 22, wherein any difference between the final accumulation mean value for each detector group and a theoretical expected mean value for the test is stored as detector group response variations in a supplementary calibration memory.

25. A method according to claim 18, whereby the presence of background B, such as that due to plate or sample phosphorescence or from intrinsic auto-fluorescence in the case of cell based assays, is detected and corrected for, by comparing the value of the transmission T derived from the index I with that derived from either J or K.

* * * * *